US008582096B2

(12) United States Patent
Chen et al.

(10) Patent No.: US 8,582,096 B2
(45) Date of Patent: Nov. 12, 2013

(54) SYSTEM AND METHOD FOR EFFICIENT COHERENCE ANTI-STOKES RAMAN SCATTERING ENDOSCOPIC AND INTRAVASCULAR IMAGING AND MULTIMODAL IMAGING

(75) Inventors: Zhongping Chen, Irvine, CA (US); Gangjun Liu, Irvine, CA (US); Mihael Balu, Newport Beach, CA (US); Bruce Tromberg, Irvine, CA (US); Eric Olaf Potma, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 432 days.

(21) Appl. No.: 12/969,295

(22) Filed: Dec. 15, 2010

(65) Prior Publication Data
US 2011/0282166 A1 Nov. 17, 2011

Related U.S. Application Data

(60) Provisional application No. 61/288,264, filed on Dec. 18, 2009.

(51) Int. Cl.
*G01J 3/44* (2006.01)

(52) U.S. Cl.
USPC .......................................................... 356/301

(58) Field of Classification Search
USPC .............. 356/301, 310, 72–73; 600/306, 476, 600/478
See application file for complete search history.

(56) References Cited

U.S. PATENT DOCUMENTS

| | | | | |
|---|---|---|---|---|
| 7,553,450 B2 * | 6/2009 | Attar et al. | ..................... | 422/408 |
| 2005/0129362 A1 * | 6/2005 | Agrawal et al. | .................. | 385/37 |
| 2006/0139633 A1 * | 6/2006 | Puppels et al. | ................. | 356/301 |
| 2006/0146322 A1 * | 7/2006 | Komachi et al. | .............. | 356/301 |
| 2007/0088219 A1 * | 4/2007 | Xie et al. | ....................... | 600/473 |

* cited by examiner

*Primary Examiner* — Tarifur Chowdhury
*Assistant Examiner* — Abdullahi Nur
(74) *Attorney, Agent, or Firm* — Marcus C. Dawes; Daniel L. Dawes

(57) ABSTRACT

A fiber-delivered probe suitable for CARS imaging of thick tissues is practical. The disclosed design is based on two advances. First, a major problem in CARS probe design is the presence of a very strong anti-Stokes component in silica delivery fibers generated through a FWM process. Without proper spectral filtering, this component affects the CARS image from the tissue sample. The illustrated embodiments of the invention efficiently suppress this spurious anti-Stokes component through the use of a separate fiber for excitation delivery and for signal detection, which allows the incorporation of dichroic optics for anti-Stokes rejection. Second, the detection of backscattered CARS radiation from the sample is optimized by using a large core multi mode fiber in the detection channel. This scheme produces high quality CARS images free of detector aperture effects. Miniaturization of this fiber-delivered probe results in a practical handheld probe for clinical CARS imaging.

19 Claims, 16 Drawing Sheets

US 8,582,096 B2

SYSTEM AND METHOD FOR EFFICIENT COHERENCE ANTI-STOKES RAMAN SCATTERING ENDOSCOPIC AND INTRAVASCULAR IMAGING AND MULTIMODAL IMAGING

RELATED APPLICATIONS

The present application is related to U.S. Provisional Patent Application, Ser. No. 61/288,264, filed on Dec. 18, 2010, which is incorporated herein by reference and to which priority is claimed pursuant to 35 USC 119.

GOVERNMENT RIGHTS

This invention was made with government support under grants EB000293, CA091717 and RR001192 awarded by the National Institute of Health, and grant 0086924 awarded by the National Science Foundation. The government has certain rights in the invention.

BACKGROUND OF THE INVENTION

1. Field of the Invention

The invention relates to the field of methods and apparatus for using a fiber-based probe and/or fiber-based endoscope for coherent anti-Stokes Raman scattering (CARS) imaging of a sample.

2. Description of the Prior Art

Nonlinear optical microscopy is a powerful imaging approach with applications found in areas as diverse as biology, medicine, and physics. Nonlinear optical microscopy includes the techniques of two-photon excited fluorescence (TPEF), second harmonic generation (SHG) and coherent anti-Stokes Raman scattering (CARS) microscopy. Coherent anti-Stokes Raman spectroscopy, also called coherent anti-Stokes Raman scattering spectroscopy (CARS), is a form of spectroscopy used primarily in chemistry, physics and related fields. It is sensitive to the same vibrational signatures of molecules as seen in Raman spectroscopy, typically the nuclear vibrations of chemical bonds. Unlike Raman spectroscopy, CARS employs multiple photons to address the molecular vibrations, and produces a signal in which the emitted waves are coherent with one another. As a result, CARS is orders of magnitude stronger than spontaneous Raman emission. CARS is a third-order nonlinear optical process involving three laser beams: a pump beam of frequency $\omega_p$, a Stokes beam of frequency $\omega_S$ and a probe beam at frequency $\zeta_{pr}$. These beams interact with the sample and generate a coherent optical signal at the anti-Stokes frequency $(\omega_p-\omega_S+\omega_{pr})$. The latter is resonantly enhanced when the frequency difference between the pump and the Stokes beams $(\omega_p-\omega_S)$ coincides with the frequency of a Raman resonance, which is the basis of the technique's intrinsic vibrational contrast mechanism.

This imaging approach as gained enormous popularity in biomedical imaging of tissues in vivo, because it provides high resolution images at fast imaging acquisition rates. Moreover, nonlinear optical microscopy does not necessitate labels as it derives its contrast from endogenous structures in the tissue. Typical applications include skin and superficial tissue imaging, often in an in vitro setting. While the potential of nonlinear microscopy for in vivo imaging is high, the actual implementation of the combined nonlinear imaging approach in the clinic requires suitable fiber-delivered probes that are currently unavailable. Several kinds of fiber-delivered and endoscopic probes have already been developed, most notably probes for optical coherence tomography (OCT), second harmonic generation (SHG) and two-photon excited fluorescence (TPEF). However, a suitable fiber-delivered probe that enables CARS imaging in addition to SHG and TPEF imaging is currently lacking.

From a design point of view, the development of a fiber-delivered or endoscopic probe that supports CARS imaging imposes additional challenges to existing probe designs. The reason for this is that unlike SHG and TPEF, CARS incorporates two laser beams, called 'Pump' and 'Stokes', that both need to be guided and focused onto the sample. Finding suitable fibers that support delivery of both laser beams without compromising the image quality has been one of the design challenges.

Another design challenge is to collect the signal, emitted at the anti-Stokes wavelength, and guide that radiation through a fiber toward a photodetector. US Pat. Pub. No. 2007/0088219 "System and Method for Coherent Anti-stokes Raman Scattering Endoscopy" discloses a system and method for fiber based CARS endoscopy. This document discloses a system for guiding both the Stokes and pump wave in one optical fiber and receive the anti-Stokes signal emitted from the sample with the same fiber or different fiber. However, it is found that strong four-wave-mixing (FWM)/CARS contribution at the anti-Stokes frequency is generated in the delivery fiber under typical CARS excitation conditions. This fiber-generated FWM/CARS component forms a large background that is typically overwhelming the signal generated in the sample, and severely complicates the interpretation of the image unless removed. This major problem is not discussed in US Pat. Pub. No. 2007/0088219, and significantly limits the application of the device proposed therein. The mixing the anti-Stokes radiation generated in the delivery fiber with the CARS signal generated from the sample forms a major limitation of the existing technology. In order to get the actual CARS image of the sample, the anti-Stokes frequency generated in the delivery fiber must be filtered out before it is focused onto the sample.

BRIEF SUMMARY OF THE INVENTION

This disclosure includes a system and method using fiber-based probe and fiber-based endoscope for efficient coherent anti-Stokes Raman scattering imaging and multimodal Imaging. Coherent anti-Stokes Raman scattering (CARS) imaging is label-free imaging of various important biomolecules at submicron resolution and at fast image acquisition rates. A suitable fiber-delivered or endoscopic probe that enables CARS imaging is currently lacking. The illustrated embodiment provides a system and method for efficient CARS imaging with fiber based imaging probe. The illustrated embodiments also provide a system and method for multimodal imaging with CARS, second harmonic generation and two-photon excited fluorescence imaging.

As stated above a strong four-wave-mixing (FWM)/CARS contribution at the anti-Stokes frequency is generated in the delivery fiber under typical CARS excitation conditions. This fiber-generated FWM/CARS component forms a large background that is typically overwhelming the signal generated in the sample, and severely complicates the interpretation of the image unless removed. The illustrated embodiment provides methods for eliminating the problem of fiber-generated anti-Stokes radiation. These methods are based on effectively filtering the fiber-generated anti-Stokes radiation before the excitation beams are focused onto the sample. The CARS signal generated in the sample is then collected by either a different part of the delivery part (e.g. inner clad of a double clad fiber) or by a different fiber. This illustrated embodiment describes a scheme for a fiber-based multiphoton probe that is optimized for CARS imaging.

The advantages of the invention are twofold. First, filtering of the spurious FWM/CARS signal generated in the fiber. This aspect was not recognized in any prior art on multiphoton fiber probes. Suppression of the FWM/CARS signal is, however, crucial to CARS imaging. We achieved suppression of the FWM/CARS signal in various ways, as described below. Second, integration of fiber-based light sources with a fiber-based multiphoton probe is provided. In prior art, the specific merger of fiber-based sources with a fiber-based probe has not been made. The combination of the two results in an extremely compact device, which is portable and suitable for applications in the clinic.

The illustrated embodiment of the invention will be used for label-free tissue imaging in-situ, endoscopic imaging. The illustrated embodiment of the invention can provide insight into myelin degradation in the nervous system and in illuminating the role of lipid in mammary tumorigenesis and atherosclerosis.

In addition, the illustrated embodiment of the invention can be also use for the following applications, which is a nonexhaustive listing which is not meant to include all the aspects of utility of the illustrated embodiments:

a. Skin damage assessment. Multiphoton imaging based on SHG/TPEF has proved successful in assessing skin health and damage due to, for instance, sun exposure. Based on optical signals from collagen (SHG) and elastin (TPEF) and index has been developed that can be correlated with age and skin damage. This invention would add CARS contrast as an additional parameter for skin diagnosis. CARS not only identifies dermal adipocytes and details of subcutaneous cells, it also provides a quantitative measure of the density of structural protein in the dermis and the level of skin hydration. Based on this improved index, this probe can be used for a real time assessment of skin health of human subjects in a clinical setting.

b. Dry eye syndrome diagnosis. This invention can be used to establish whether patients with dry eyes are suffering from dry eye syndrome (DES). DES is a condition related to the malfunction of the Meibomian gland, which can be found in the eyelid. The Meibomian gland secretes a lipid tear film that prevents the eye from drying. Upon aging, Meibomian glands may shrink and alter their lipid production, leading to DES. Meibomian glands cannot be seen with standard microscopic in vivo inspection. With CARS, however, Meibomian glands are easily identified and can be assessed. This fiber probe enables a direct inspection of human subjects in vivo by gently lifting the eyelid and visualizing the superficial glands in real time, permitting a direct diagnosis of DES.

c. Food analysis. This invention would be great for inspecting the quality of surfaces of food items. For instance, the CARS modality enables one to identify the onset of 'blooming' on chocolate surfaces. Chocolate producing companies are spending millions on controlling blooming, and early identification (small lipid crystals at the chocolate surface) is an important ability in controlling this effect.

d. Photoresists. Quick inspection of photoresists films is important in quality control of these thin polymer films. CARS have proved sensitive to chemical changes at the surface. This invention would enable quick inspection by easily directing the probe to the area of interest.

e. Imaging and diagnose vascular diseases with intravascular CARS imaging and multimodal imaging.

f. Image and diagnose cancers with endoscopic CARS imaging and multimodal imaging.

More specifically, the illustrated embodiments of the invention include a method for using a fiber-based probe and/or fiber-based endoscope for coherent anti-Stokes Raman scattering (CARS) imaging of a sample comprising the steps of delivering Stokes and pump excitation beams to a fiber for scanned delivery to the sample, eliminating fiber-generated anti-Stokes radiation by removing the fiber-generated anti-Stokes signal before the Stokes and pump excitation beams are delivered to the sample, collecting the CARS signal backscattered from the sample, and returning the CARS signal to a detector by utilizing a different portion of the fiber for the CARS signal or by utilizing a different fiber for the CARS signal.

The method further includes multimodal imaging with second harmonic generation imaging, two-photon excited fluorescence imaging and coherent anti-Stokes Raman scattering (CARS) imaging.

The step of collecting the CARS signal backscattered from the sample includes the step of collecting the CARS signal in a fiber separate from the fiber through which the Stokes and pump excitation beams are delivered, or a separate portion of the fiber through which the Stokes and pump excitation beams are delivered.

The step of eliminating or suppressing the fiber-generated anti-Stokes signal includes the step of suppressing the anti-Stokes signal through the use of a dichroic beam splitter for anti-Stokes rejection or through the use of a special fiber for anti-Stokes rejection.

The step of returning the CARS signal to a detector by utilizing a different portion of the fiber for the CARS signal or by utilizing a different fiber for the CARS signal includes the step of using a large core multimode fiber to transmit the CARS signal to the detector.

The illustrated embodiments also include an apparatus which has a source of a Stokes and pump excitation beam, a delivery fiber optically coupled to the source, a dichroic beam splitter optically coupled to the delivery fiber, any fiber-generated anti-Stokes signal being suppressed before the Stokes and pump excitation beams are delivered, a scanner for scanning a transmission beam from the dichroic beam splitter into a sample, optics for collecting backscattered an anti-Stokes signal from the sample, a collection fiber optically coupled to the optics, and a detector optically coupled to the collection fiber to detect the backscatter anti-Stokes signal.

In one embodiment the delivery fiber and collection fiber comprise separate optical fibers, while in another embodiment the delivery fiber and collection fiber comprise separate portions of the same optical fiber.

The delivery fiber has a core, a inner clad and an outer clad, where the core suppresses the anti-Stokes signal and where the inner clad transmits the anti-Stokes signal.

In one embodiment the fiber is a photonic crystal fiber, photonic bandgap fiber or microstructure fiber with its core designed to suppress the anti-Stokes signal.

In one embodiment the core comprises a core which is doped to absorb and filter out the anti-Stokes signal.

In one embodiment the core comprises a thin film coated on a distal end of the core that filters out the anti-Stokes signal.

In one embodiment the core comprises a device that redirects the anti-Stokes signal. The device comprises a fiber Bragg grating to reflect the anti-Stokes signal.

In one embodiment the core comprises a filter segment that filters out the anti-Stokes signal.

In one embodiment the apparatus further includes a transparent endoscopic tube in which the delivery fiber and collection fiber and scanner are disposed, and means for rotating the delivery fiber and collection fiber. The scanner includes a GRIN lens optically coupled to the delivery fiber and collection fiber and a prism optically coupled to the GRIN lens for side scanning through a distal end of the tube.

In one embodiment the apparatus further includes a transparent endoscopic tube in which the delivery fiber and collection fiber and scanner are disposed, a GRIN lens optically coupled to the delivery fiber and collection fiber and a prism optically coupled to the GRIN lens for side scanning through a distal end of the tube, and where the scanner comprises a motor for rotating the prism.

In one embodiment apparatus further includes a linear translational motor coupled to the delivery fiber and collection fiber for translating the delivery fiber and collection fiber within the tube.

In one embodiment the apparatus further includes a transparent endoscopic tube in which the delivery fiber and collection fiber and scanner are disposed, where the scanner comprises a mirror, a MEMS scanner for moving the mirror and a lens optically coupled to the mirror.

In one embodiment the apparatus the delivery fiber and collection fiber comprise a fiber bundle having a central fiber for transmission of the Stokes and pump signal and a plurality of outer fibers for transmission of the anti-Stokes signal.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The invention can be better visualized by turning now to the following drawings wherein like elements are referenced by like numerals.

BRIEF DESCRIPTION OF THE DRAWINGS

FIGS. 11a-11c are CARS micro-photographic images of thick tissue samples ex vivo. FIG. 11a shows the small adipocytes of mouse ear skin. FIG. 11b shows the adipocytes of subcutaneous layer of rabbit skin tissue. FIG. 11c shows the meibomian gland in mouse eyelid. All of the images were acquired in 2 s. The scale bar is 50 μm.

The invention and its various embodiments can now be better understood by turning to the following detailed description of the preferred embodiments which are presented as illustrated examples of the invention defined in the claims. It is expressly understood that the invention as defined by the claims may be broader than the illustrated embodiments described below.

DETAILED DESCRIPTION OF THE PREFERRED EMBODIMENTS

The illustrated embodiments of the invention provide a method for eliminating the problem of fiber-generated anti-Stokes radiation. The various embodiments of the method is based on effectively filtering the fiber-generated anti-Stokes radiation before the excitation beams are focused onto the sample. The CARS signal generated in the sample is then collected by either a different portion of the delivery device (e.g. inner clad of a double clad fiber) or by a different fiber.

The illustrated embodiments of the invention describe a scheme for a fiber-based multiphoton probe that is optimized for CARS imaging.

The illustrated embodiments of the invention include two aspects. First, it includes the filtering of the spurious FWM/CARS signal generated in the fiber. This aspect was not recognized in any prior art on multiphoton fiber probes. Suppression of the FWM/CARS/CARS signal is, however, crucial to CARS imaging. We achieved suppression of the FWM/CARS signal in various ways, as described below. Second, the illustrated embodiments include the integration of fiber-based light sources or other compact laser source with a fiber-based multiphoton probe. In prior art, the specific merger of compact fiber-based sources with a fiber based probe has not been made. The combination of the two results in an extremely compact device, which is portable and suitable for applications in the clinic.

Figure 1:
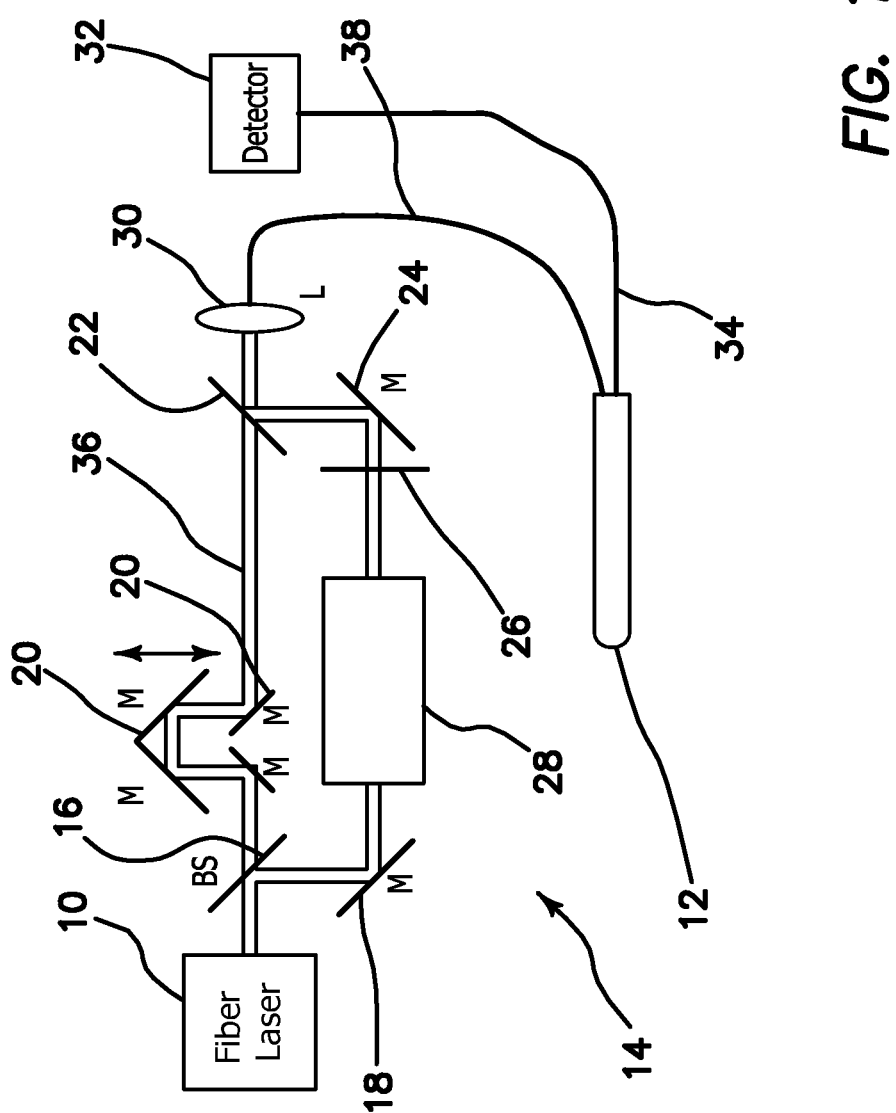
FIG. 1 a diagram of a CARS multiphoton imaging system with fiber laser source and fiber probe.

Consider the general organization of the disclosed CARS multiphoton imaging system with a fiber laser source 10 and fiber probe 12. FIG. 1 is a block diagram of a CARS multiphoton imaging system, generally denoted by reference numeral 14, with fiber laser 10 as a source and fiber-based imaging probe 12. The CARS imaging laser source 10 may be a laser source plus a nonlinear frequency conversion step to produce a second beam that is spectrally tunable. The nonlinear frequency conversion step could be implemented by use of: 1) a highly nonlinear fiber; 2) a fiber plus a second harmonic generation (SHG) crystal; or 3) a fiber-based optical parametric oscillator (OPO). The system and method disclosed here may use either a femtosecond or picosecond laser source 10 at a frequency $\omega_p$ as a pump laser and a Stokes beam laser source 28, which includes a wavelength/frequency converting element such as a fiber based super continuum generator, such as a highly nonlinear fiber; a fiber plus a second harmonic generation (SHG) crystal; or a fiber-based optical parametric oscillator (OPO). The light from pump laser 10 is split by beam splitter 16 and directed by mirror 18 into Stokes beam laser source 28. The remaining portion of the light is directed by a system of mirrors 20 along an optical path 36 of predetermined path length. The output of Stokes beam laser source 28 at the frequency $\omega_S$ is filtered by filter 26 and directed by mirror 24 and combined with the light in path 36 through dichroic mirror 22 to a lens or lensing system 30 to provide light at frequency $\omega_p$ and $\omega_S$. The combined beam is delivered through an optic fiber 38 to a probe 12. Light at the anti-Stokes frequency $2\omega_p - \omega_S$ is produced by the sample. The return signal at anti-Stokes frequency from the sample is delivered via optic fiber 34 to a detector 32.

The disclosed system and method may also be combined with a system and method for CARS endoscopic imaging with other kinds of imaging techniques such as SHG, TPEF and OCT for multimodal endoscopic imaging.

Figure 4:
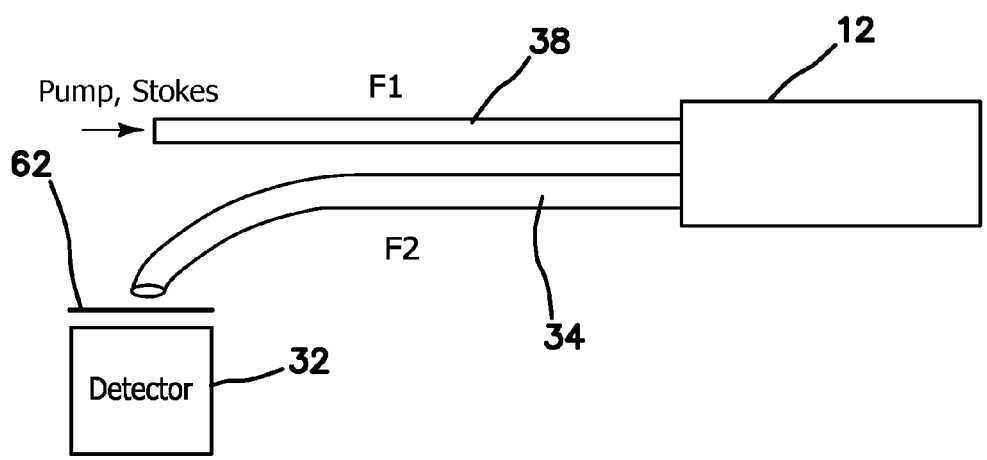
FIG. 4 is a diagram of a CARS multiphoton imaging system with the endoscopic fiber probe of FIGS. 3a-3c.

One aspect of the probe design is the way in which the light is delivered and collected. The probe 12 incorporates: a. An optical guide for delivery of pump and Stokes excitation laser pulses; and b. An optical guide for collecting the CARS and multiphoton signals generated in the sample. FIG. 4 is a schematic diagram of a CARS endoscopic probe 12 for CARS endoscope application, where delivery fiber 38 provides the Stoke/pump signal to probe 12 and the Anti-Stokes backscattered signal is provided on data collection fiber 34, filtered by filter 62 and input into detector 32.

In addition, the probe 12 incorporates a device for filtering the FWM/CARS light, a device for scanning the laser beams, and elements for focusing the light onto the sample. The filtering of the FWM/CARS light may be realized by a dichroic beam splitter, an optical filter or a specially designed fiber. The scanning device may be galvanometric scanner, piezoceramic tube, magnet driving scanner or Microelectromechanical systems (MEMS) scanning mirror. The focusing element may be microscope objective, optical lens or gradient index lens. The specific embodiments of FIGS. 2, and 3a-3c provide clarifying examples.

Figure 2:
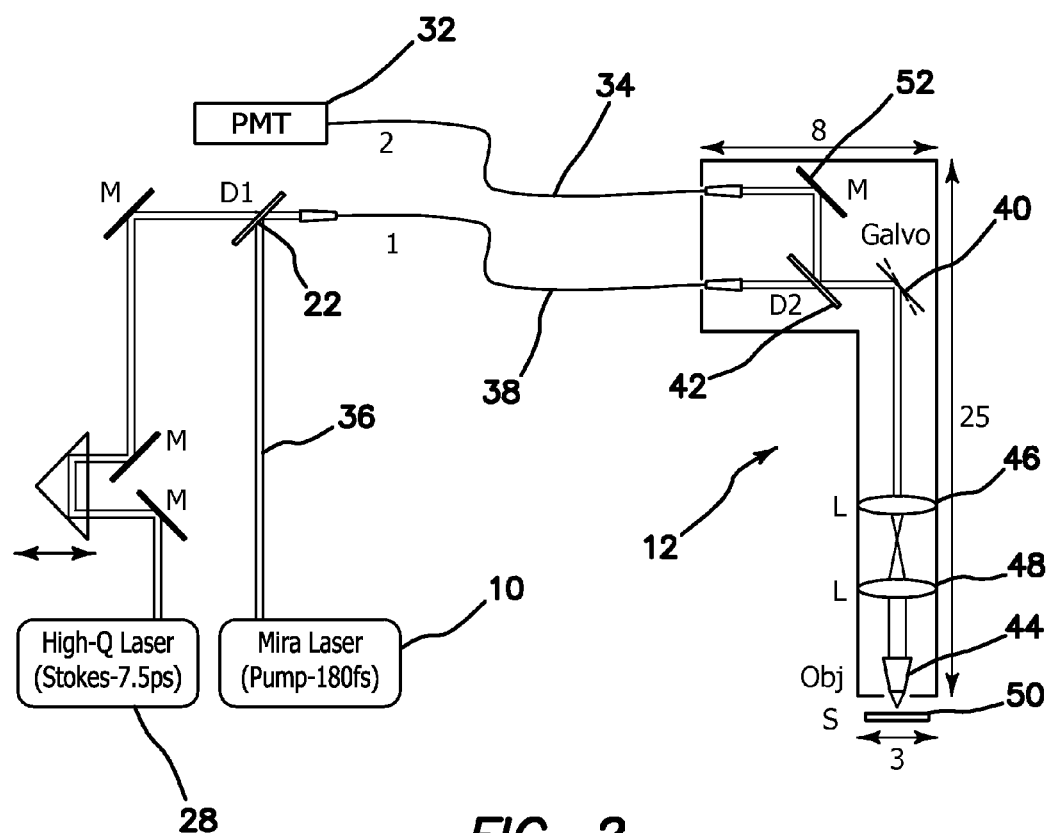
FIG. 2 is a diagram of a CARS multiphoton imaging system with fiber laser source and fiber probe showing greater detail concerning the fiber probe.

One embodiment of the invention is shown in FIG. 2. FIG. 2 shows a CARS multiphoton microscope with a hand-held imaging probe 12. A Ti:Sapphire oscillator 10, delivering 280 fs pulses at 76 MHz, with a wavelength tunable in the 750-920 nm range, is used as the pump beam in the CARS process. The Stokes beam was derived from a 76 MHz mode-locked laser source 28 which produces 7.5 ps-pulsed 1064 nm light. The two laser sources were synchronized using a conventional active feedback scheme. The pump and Stokes beams are collinearly overlapped using 1000 nm long pass dichroic mirror 22. The handheld probe 12 incorporates a delivery fiber 38, scanning device 40, an objective lens 44 and a separate fiber 34 for signal collection. After passage through the delivery fiber 38, the pulses were directed to a 760 nm long pass dichroic mirror 42. Laser beam scanning is achieved with a galvanometric scanner 40 (MEMS mirror scanner) and a scan lens 46 and tube lens 48 to project the excitation light onto an objective lens 44. The back-scattered CARS signal from sample 50 is collected by the focusing objective 44, separated from the excitation beams by the dichroic mirror 42 and directed by mirror 52 via optic fiber 34 to a photomultiplier tube 32. The scan and the data collection were controlled by software.

Figure 3A:
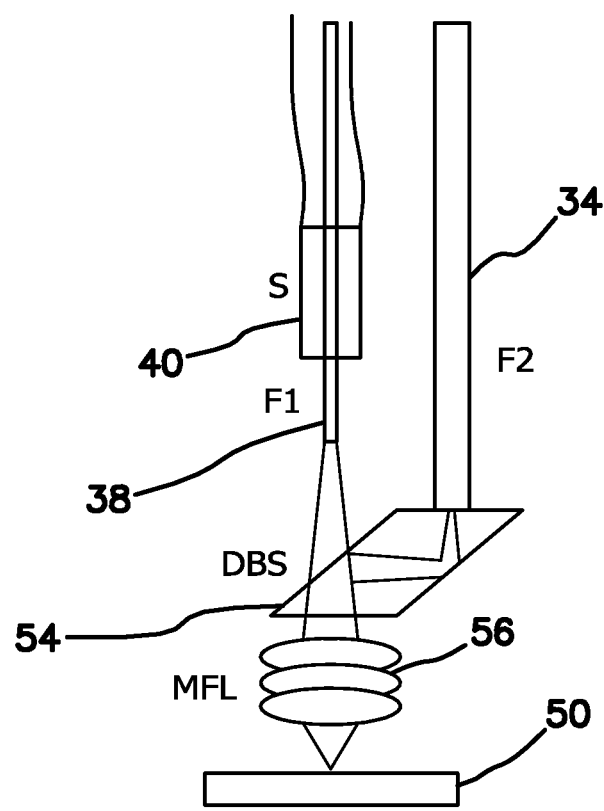
FIGS. 3a-3c are diagrams of various embodiments an endoscopic fiber probe.
Figure 3B:
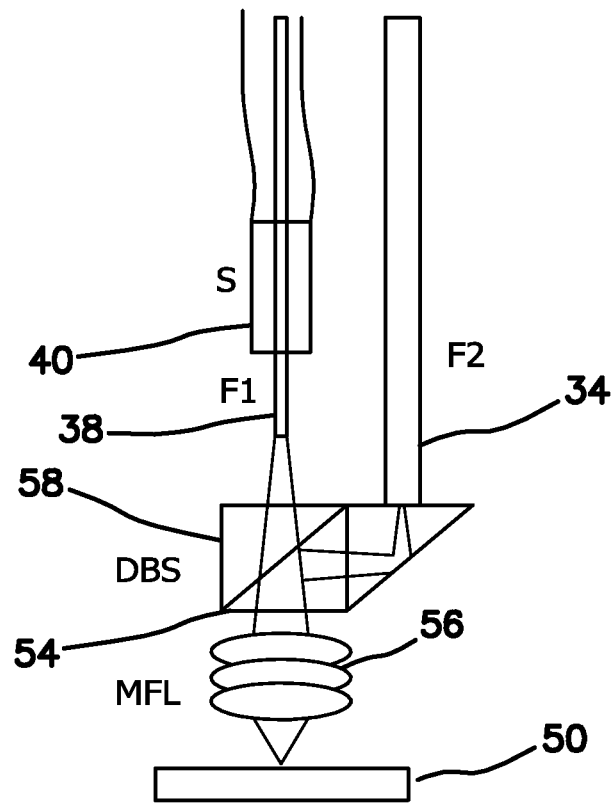
Figure 3C:
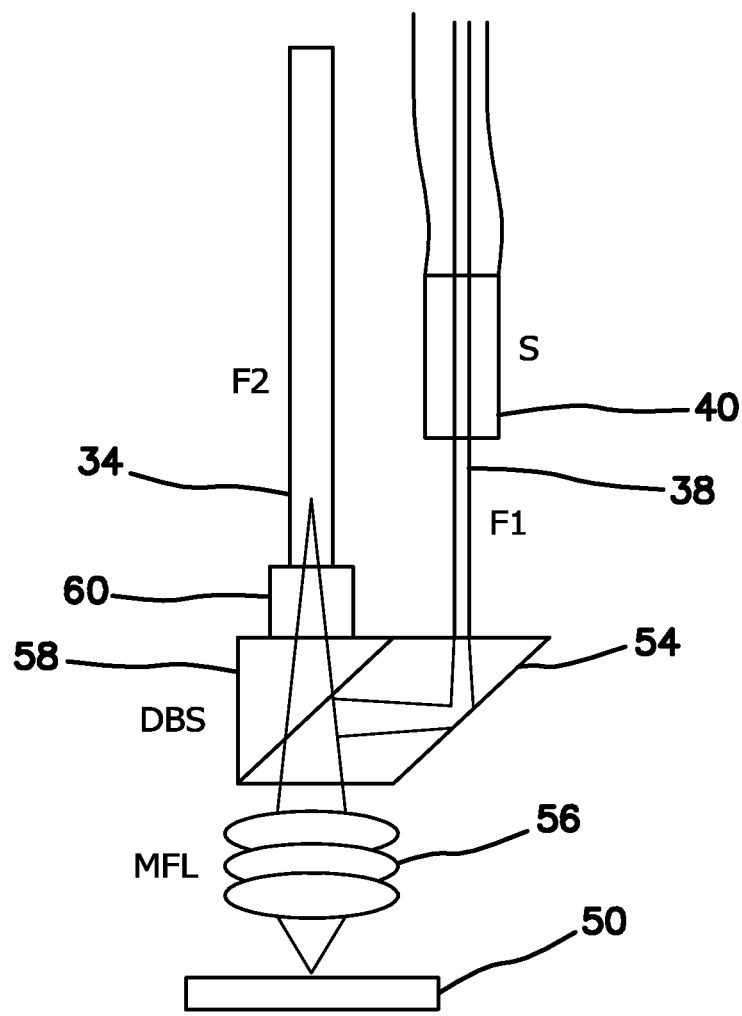

Another embodiment of the CARS endoscopic probe 12 for a CARS endoscope application is schematically depicted in FIGS. 3a-3c. The scanner 40 is realized, for example, using piezoceramic tubes, a magnetically driven scanner or any other kind of optical scanner now known or later devised. The Stokes and pump beam delivery fiber 38 takes its input from scanner 40. The backscattered light is collected into the CARS signal collection fiber 34. Light from delivery fiber 38 is provided to a dichroic beam splitter 54. The dichroic beam splitter 54 filters the anti-Stokes single generated from the delivery fiber 38 before it impinges on the sample 50. The dichroic beam splitter 54 also redirects the CARS signal from the sample 50 to the collection fiber 34. A miniature focusing lens system 56 focuses the light from beam splitter 54 onto the sample 50.

The embodiment of FIG. 3b differs from that of FIG. 3a by the combination of a prism 58 between the output of delivery fiber 38 and beam splitter 54 for the purpose of optimized packaging.

The embodiment of FIG. 3c differs from that of FIGS. 3a and 3b by exchanging the location of the delivery fiber 38 and the location of the collection fiber 34 and providing prism 58 to pass the backscattered signal and by the combination of a lens 60 between the prism 58 and collection fiber 34 for the purpose of increasing the signal collection efficiency.

Figure 5:
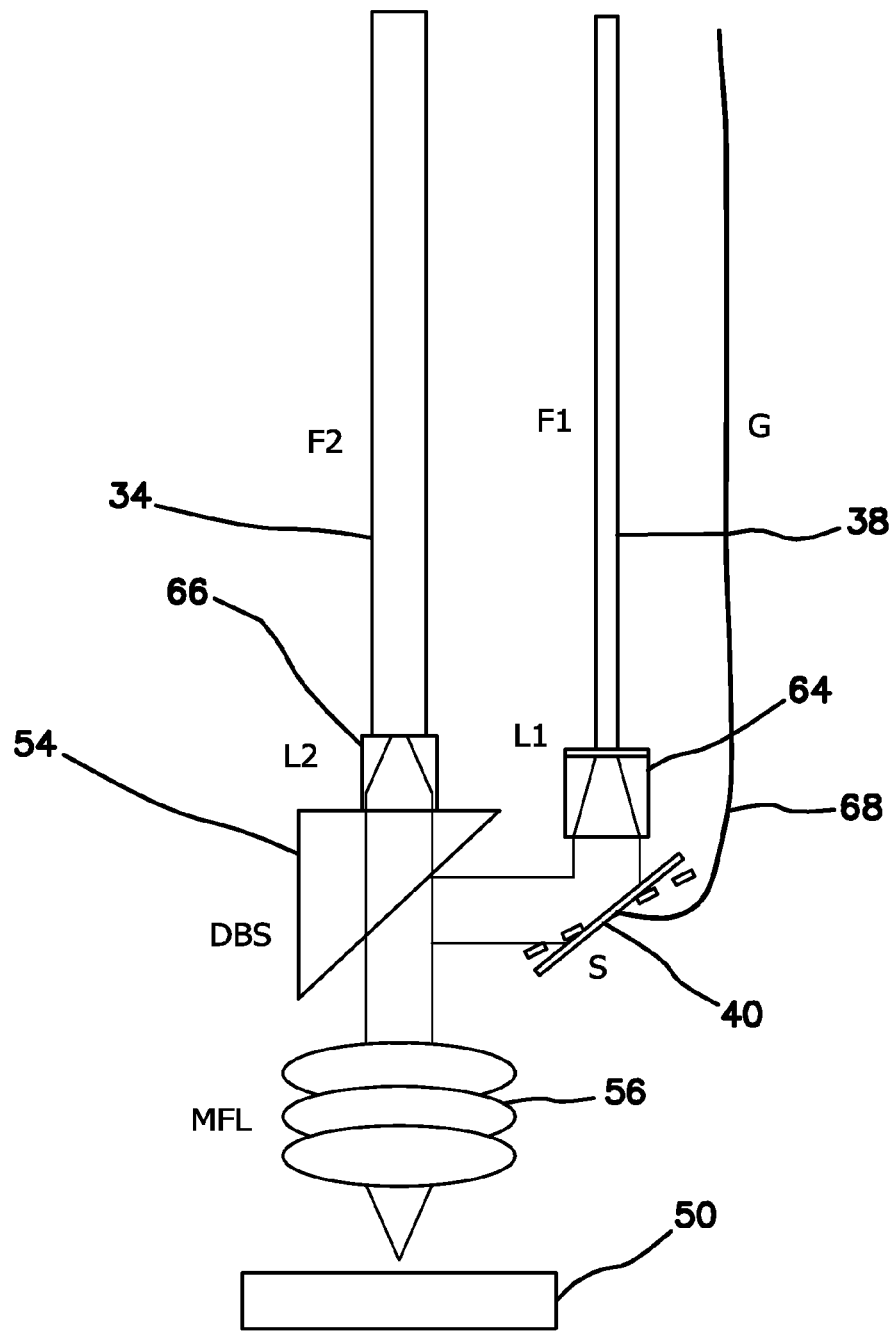
FIG. 5 is a diagram of another embodiment a CARS multiphoton imaging system with the endoscopic fiber probe with the scanner optically coupled to the dichroic beam splitter.

FIG. 5 is a schematic of another embodiment of the CARS imaging endoscopic probe 12. In this embodiment beam scanner 40 is provided to scan the light from Stokes and pump beam delivery fiber 38 and lens 64, which is then delivered to beam splitter 54. Scanner 40 includes, for example, a microelectromechanical scanning mirror controlled by a computer or control circuitry (not shown) to which it is coupled by wire 68. The dichroic beam splitter 54 filters the anti-Stokes signal produced from the delivery fiber 38 before it impinges on the sample 50. The dichroic beam splitter 54 redirects the CARS signal from the sample 50 to lens 66 and then to the collection fiber 34. The embodiment of the designed endoscopic probe in FIG. 5 is used in the system of in FIG. 4.

The illustrated embodiment include different configurations of the delivery and collection fibers 38, 34. In the examples below we show fiber schemes in which the delivery fiber 38 and the collection fiber 34 are integrated into one fiber or one bundle. No bulky dichroic component is needed at the distal end of the endoscope probe 12, which significantly reduces the probe size. A first embodiment is diagrammatically shown in the end plan view of FIG. 6*a* where a distal end of a double clad fiber 70 includes a core adapted for CARS endoscopic probe 12. The fiber 70 includes an optical core 72 with a concentrically enveloping inner cladding 74 within a concentrically enveloping outer cladding 76. The core 72 is arranged and configured to carry the Stokes and pump frequency but not the Anti-Stokes signal. The inner cladding 74 carries the Anti-Stokes signal. The CARS signal produced by the sample will be collected by the inner clad 74 of the DCF 70.

Figure 6A:
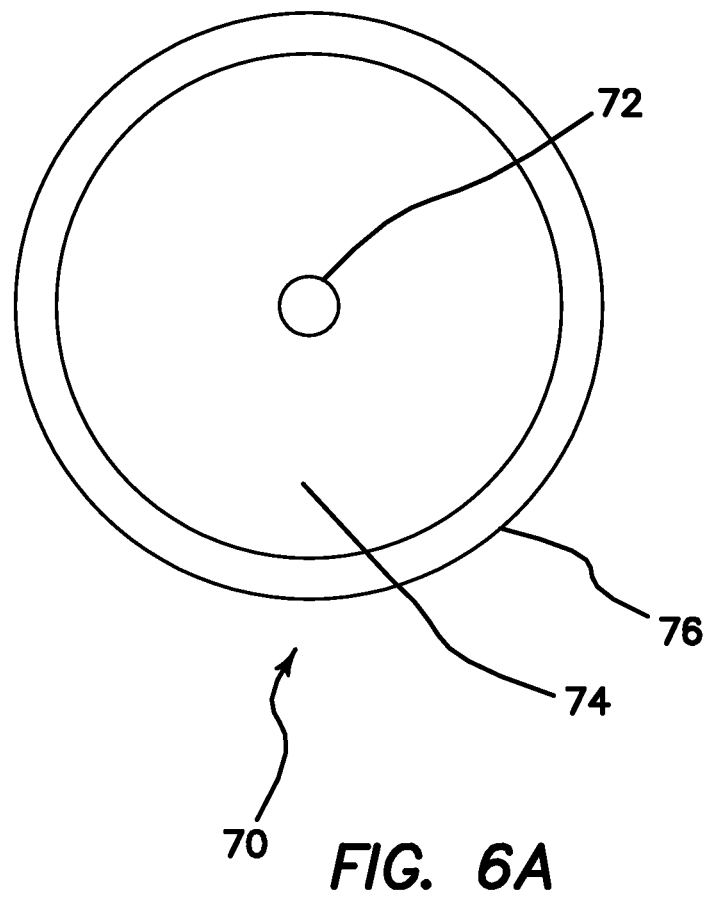
FIG. 6a is a perpendicular cross sectional view of the double clad large area core photonic crystal fiber of the illustrated embodiments of the endoscopic system.
Figure 6B:
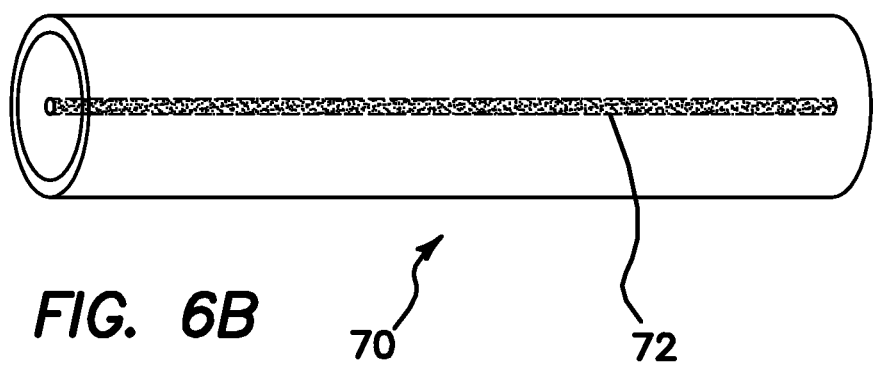
FIG. 6b is a perspective view of the fiber of FIG. 6a in which the core is doped to suppress the anti-Stokes signal.

FIG. 6*b* is a perspective diagram of an embodiment of fiber 70 of FIG. 6*a* where the core is specially doped to absorb and filter out the anti-Stokes frequency.

Figure 6C:
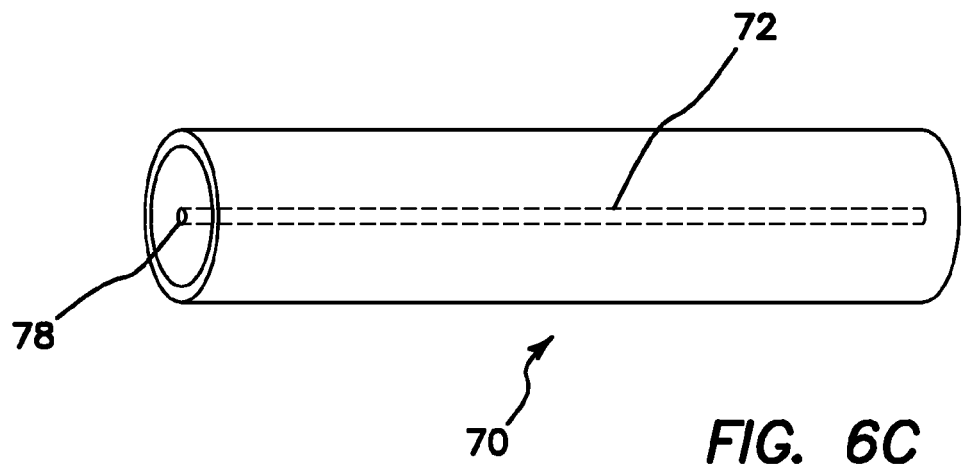
FIG. 6c is a perspective view of the fiber of FIG. 6a in which the distal end of the core is provided with a thin film to suppress the anti-Stokes signal.

FIG. 6*c* shows an embodiment of double clad fiber 70 with a thin film 78 coated on the core 72 at its distal end that filters out the anti-Stokes frequency.

Figure 6D:
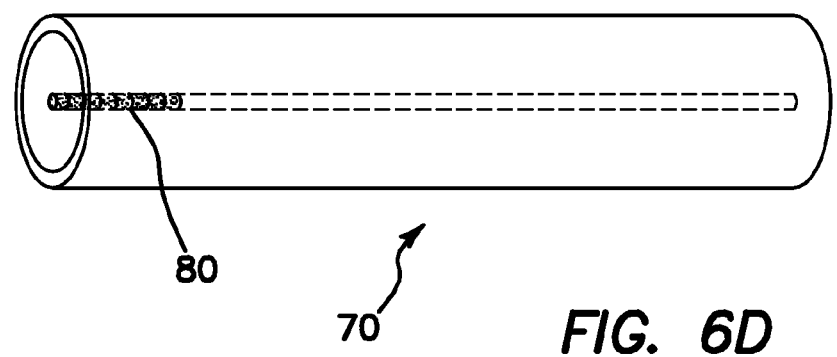
FIG. 6d is a perspective view of the fiber of FIG. 6a in which the core is provided with a Bragg grating to redirect the anti-Stokes signal.

An embodiment of core 72 of the DCF 70 may be fabricated with a special device that may redirect the anti-Stokes frequency, for example, a fiber Bragg grating to reflect the anti-Stokes frequency as shown in FIG. 6*d*. FIG. 6*d* is a diagram of double clad fiber 70 with a fiber Bragg grating 80 fabricated inside at least a distal portion of core 72 that filters out the anti-Stokes frequency.

Figure 6E:
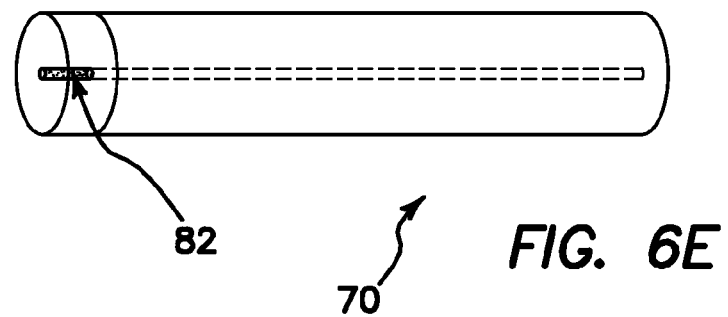
FIG. 6e is a perspective view of the fiber of FIG. 6a in which the core is provided with a filtering segment to suppress the anti-Stokes signal.

FIG. 6*e* is a diagram of an embodiment of double clad fiber 70 fused with a filter segment 82 that filters out the anti-Stokes frequency. Segment 82 is a short segment of special fiber that may assume any one of the embodiments of FIGS. 6*a-b*.

Figure 6F:
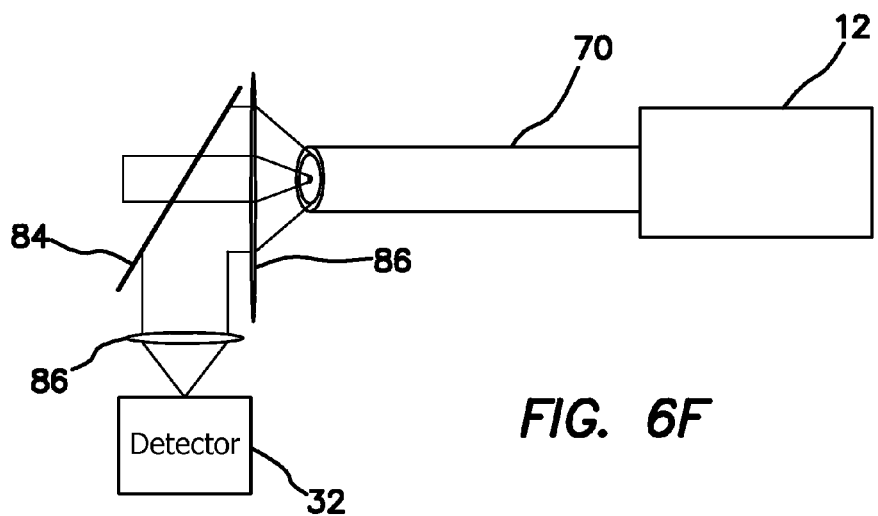
FIG. 6f is a diagram showing the use of the fiber of FIG. 6a in a fiber endoscopic system.

FIG. 6*f* is a schematic of an embodiment of the specially designed double clad fiber 70 for a CARS endoscope application in which a dichroic beam splitter 84 is provided at the output of fiber 70 in combination with lensing system 86 to provide Stokes and pump light to the probe 12 and to guide the CARS signal to detector 32 respectively.

Figure 6G:
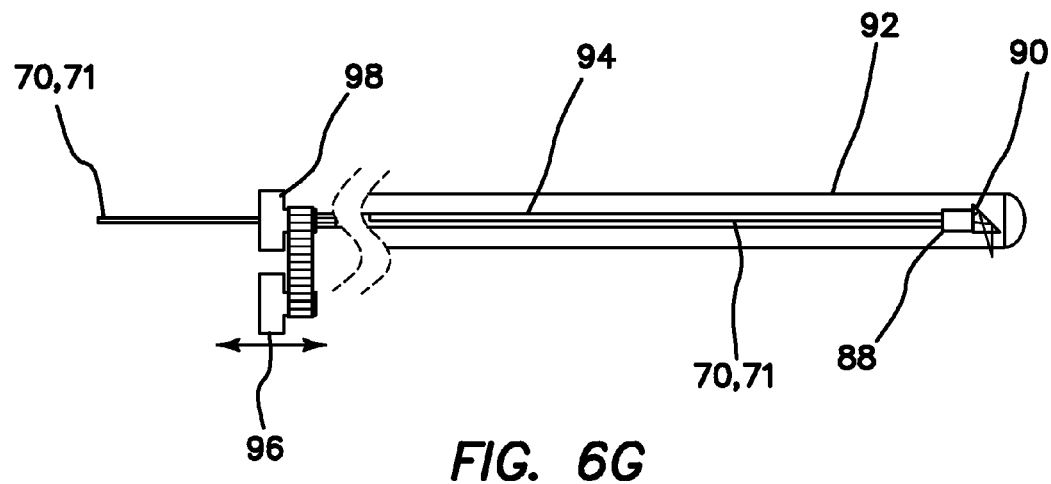
FIG. 6g is a diagram showing the use of the fiber of FIG. 6a in a fiber endoscopic system in which the fiber is rotated and combined with a GRIN lens and prism to provide side scanning.

FIG. 6*g* is a schematic of another embodiment of endoscopic probe 12 with the specially designed fiber 70 or 71 shown in FIGS. 6*a*-6*e* or FIG. 7 discussed below. A gradient index (GRIN) lens 88 is coupled to an prism 90 to provide distal side illumination through a fluorinated ethylene propylene (FEP) transparent tube 92. Lens 88 is coupled to a hollow torqueable, flexible guidewire 94 telescopically disposed in the central lumen of tube 92. Also telescopically disposed in the central lumen of guidewire 94 is optic fiber 70 or 71. The proximal end of guidewire 94 is coupled to an external motor 96 which rotates guidewire 94 and hence lens 88 and prism 90 within tube 92. Optical coupling is provided at the proximal end of fiber 70, 71 to a fiber rotation joint 98 optically coupled to a nonrotating fiber 70, 71 which is part of the CARS endoscopic system 14.

Figure 6H:
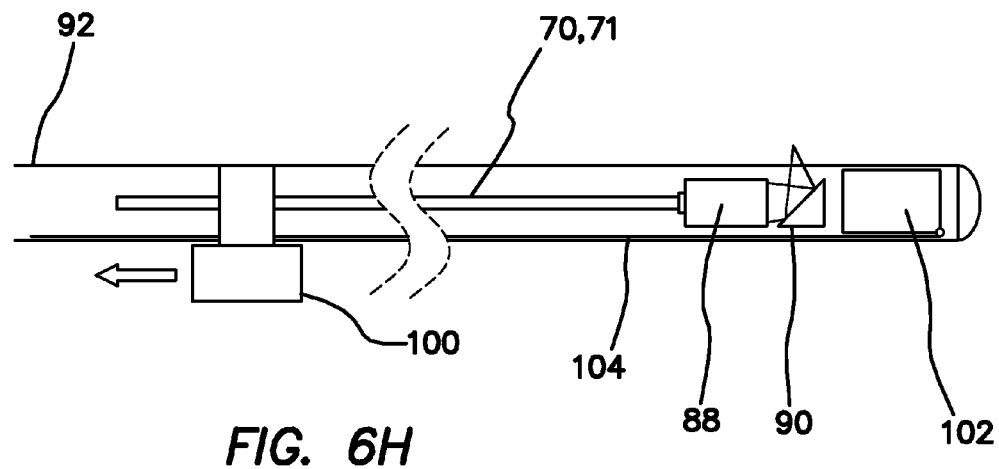
FIG. 6h is a diagram showing the use of the fiber of FIG. 6a in a fiber endoscopic system combined with a GRIN lens and prism and in which the prism is rotated and to provide side scanning and where the fiber may be linearly translated within the endoscope.

FIG. 6*h* is a diagram of an embodiment of endoscopic probe 12 with the specially designed fiber 70, 71 shown in FIGS. 6*a*-6*e* or FIG. 7. The probe 12 of FIG. 6*g* has been modified to provide the rotation to prism 90 using a distally position MEMS motor 102 coupled to prism 90 in tube 92. Fiber 70, 71 does not rotate but is proximally coupled to linear translational motor 100 so that fiber 70, 71, lens 88, prism 90 and motor 102 are selectively bidirectionally translated within transparent tube 92 under control of the user.

Figure 6I:
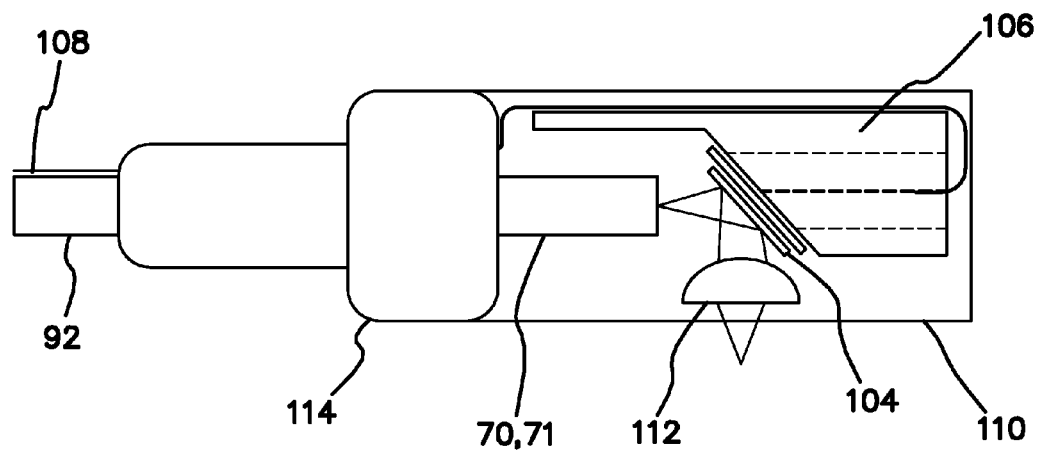
FIG. 6i is a diagram showing the use, of the fiber of FIG. 6a in a fiber endoscopic system combined with a MEMs scanner driving a mirror optically coupled to a lens to provide side scanning.

FIG. 6*i* is a diagram of another embodiment of endoscopic probe 12 with the specially designed fiber 70, 71 shown in FIGS. 6*a*-6*e* or FIG. 7. Fiber 70, 71 is telescopically disposed through tube 92 into a fitting 114 and extends below the distal end of fitting 114 into a transparent outer sheath 110. A MEMS scanner 106 is mounted in sheath 110 and carries a mirror 104, which selectively redirects the light in fiber 70, 71 to a lens 112 for side scanning. MEMS scanner 106 is coupled to a wire 108 which is led proximally to a computer or control circuit (not shown) for controlling the scanning operation.

Figure 7A:
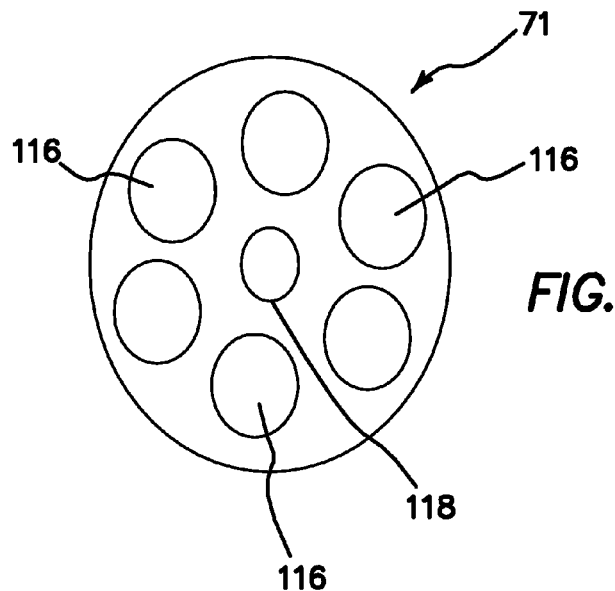
FIG. 7a is a perpendicular cross sectional view of a fiber bundle where the delivery core is provided as a central fiber and surrounded by a plurality of collection fibers.

FIG. 7 is a distal end plan view of a fiber 71 designed for CARS endocope. Several individual fibers 116 are included in the fiber 71 and a center fiber 118 carries the pump and Stokes beam. The outer fibers 116 around the center fiber 118 carry the CARS signal. The center fiber 118 is specially designed and may assume any one of the embodiments of FIGS. 6*a*-6*e*.

Figure 7B:
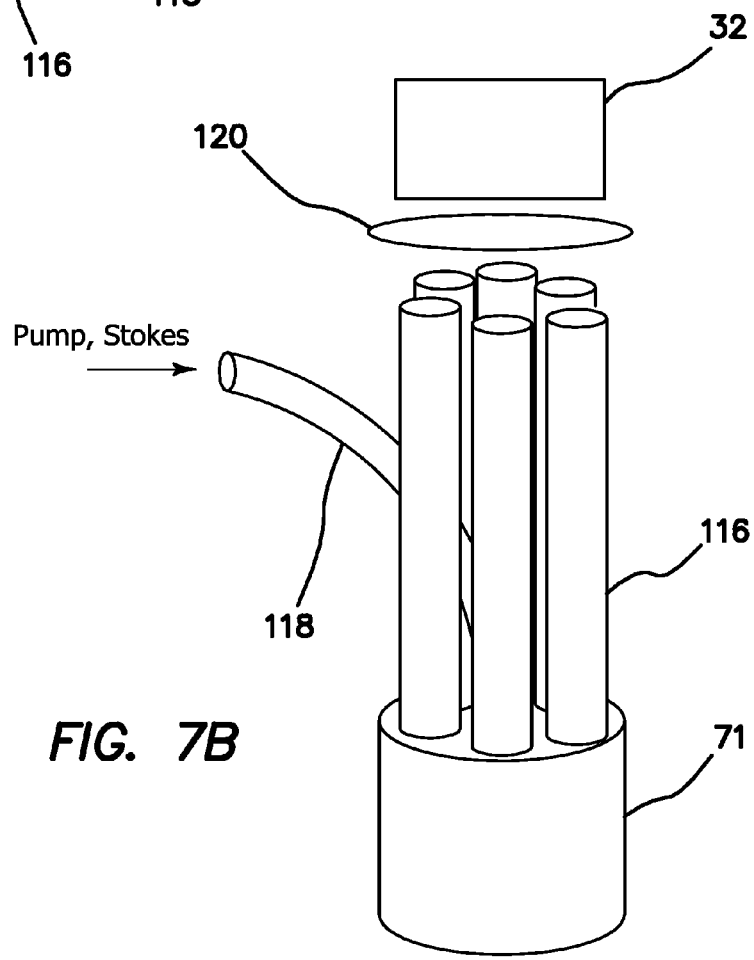
FIG. 7b is a perspective view of a proximal end of the bundle of FIG. 7a where the collection fibers are optically coupled to a lens and detector and the delivery fiber is separately coupled to a source of the Stokes and pump signals.

FIG. 7*b* is a schematic of an embodiment of the use of fiber 71 for a CARS endoscope application. Outer fibers 116 are each optically coupled to a lens 120 and thence to detector 32. Center fiber 118 is optically coupled to the Stokes and pump signal.

Figure 8A:
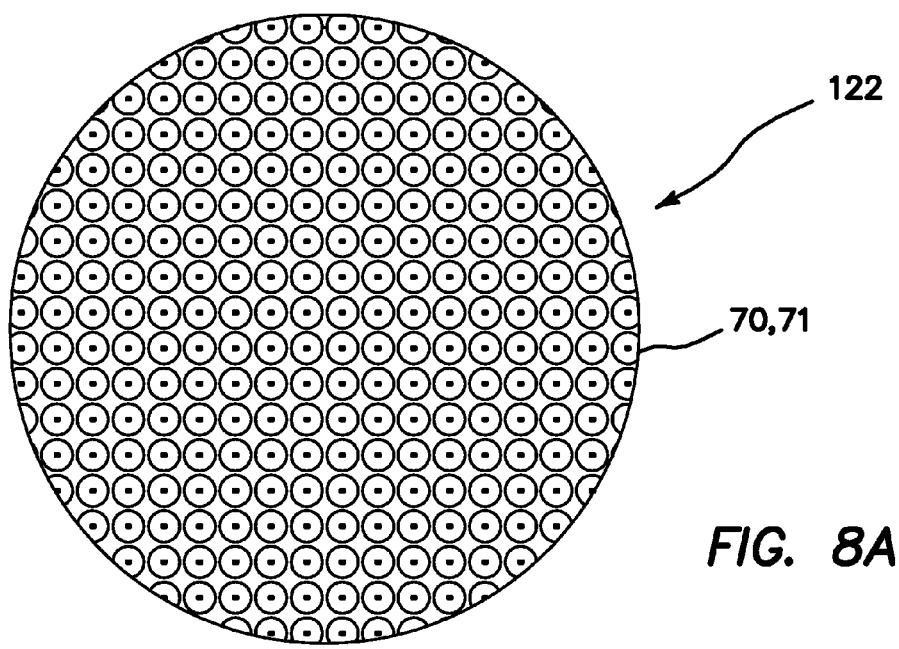
FIG. 8a is a perpendicular cross sectional view of a fiber bundle where a plurality of fibers of FIG. 6a are combined in a bundle.
Figure 8B:
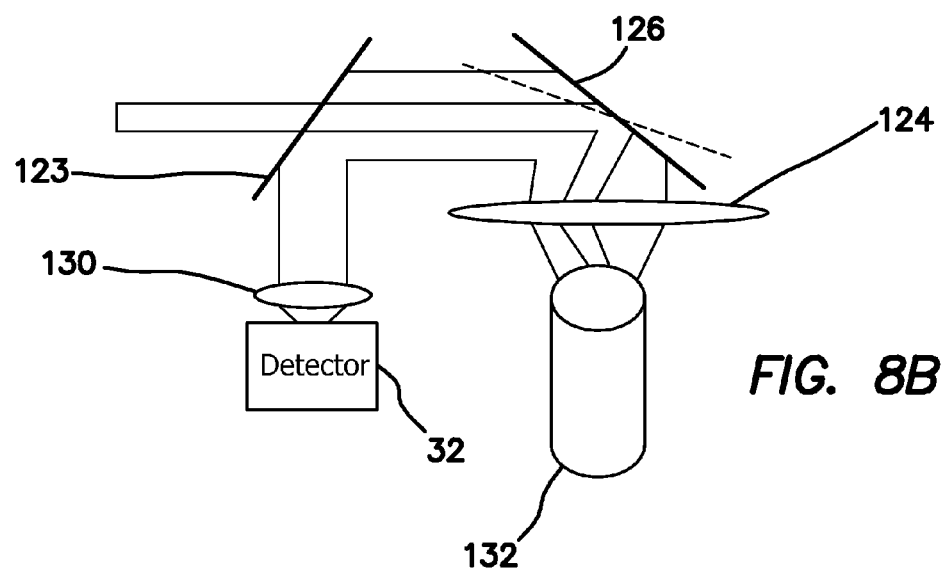
FIG. 8b is a diagram where the fiber bundle of FIG. 8a is employed in a fiber endoscopic system.

The embodiments of FIGS. 6*a*-6*e* and 7 can be expanded to include a plurality of such fibers 70, 71 in a fiber bundle 122 as shown in the end plan view of FIG. 8*a*. Bundle 122 is employed in the design schematically shown in FIG. 8*b* where the light transmitted through bundle 122 is focused by lens 124 to a scanner 126, which in turn receives the Stokes and pump signal from dichroic beam splitter 128 and returns the anti-Stokes signal to dichroic beam splitter 128 and thence to lens 130 and detector 32.

Different kinds of large core fibers may be employed in the various embodiments disclosed above. For example, a fused silica single mode fiber (SMF), a double-clad photonic crystal fiber (DC PCF) and a large mode area PCF (LMA PCF) may each be employed. While the spectral broadening was not a concern for the individual pump and Stokes pulses in photonic crystal fiber (PCF) fibers, new frequency components may arise when the pump and Stokes signals are temporally overlapped in the fiber as a result frequency mixing. In particular, for fibers that support phase-matching over a wide bandwidth, anti-Stokes frequency components can be generated through a FWM/CARS process in the fiber. To suppress such FWM/CARS effects, PCF fibers were used that do not support phase-matching of the frequency components shifted by ~3000 cm$^{-1}$ relative to the zero dispersion wavelength of the fiber. Hence, the illustrated fibers fulfill the condition:

$$(2\beta_p - \beta_S + \beta_{as}) \cdot L = \Delta\beta \cdot L \geq |\pi|$$

where $\beta_p$, $\beta_S$ and $\beta_{as}$ are the wave vectors of the pump, Stokes and anti-Stokes components, respectively, and L is the length of the fiber over which the frequency components remain temporally overlapped. Under these conditions, no coherent anti-Stokes generation is expected through a nonresonant FWM/CARS process.

Figure 9A:
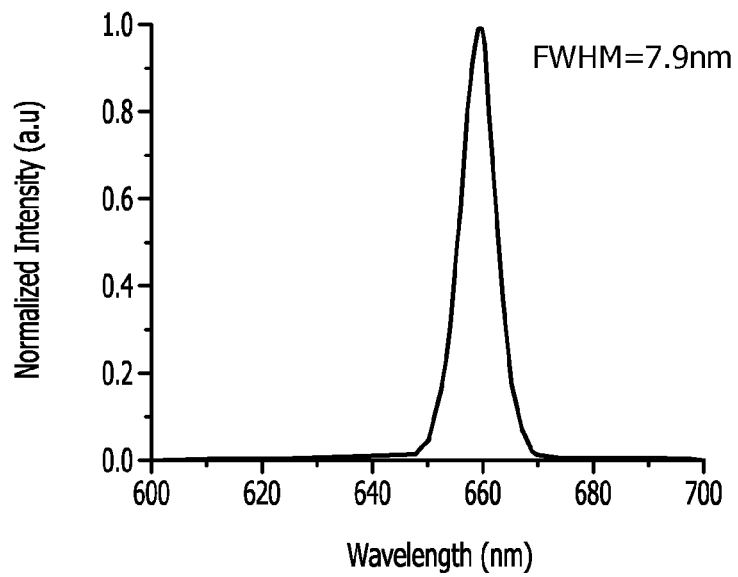
FIG. 9a is a graph of the Anti-Stokes four-wave-mixing signal measured at the output of the large area core photonic crystal fiber output of FIG. 6a and FIG. 9b is a graph of the Anti-Stokes four-wave-mixing signal measured at the output of a silica single mode fiber (SMF).
Figure 9B:
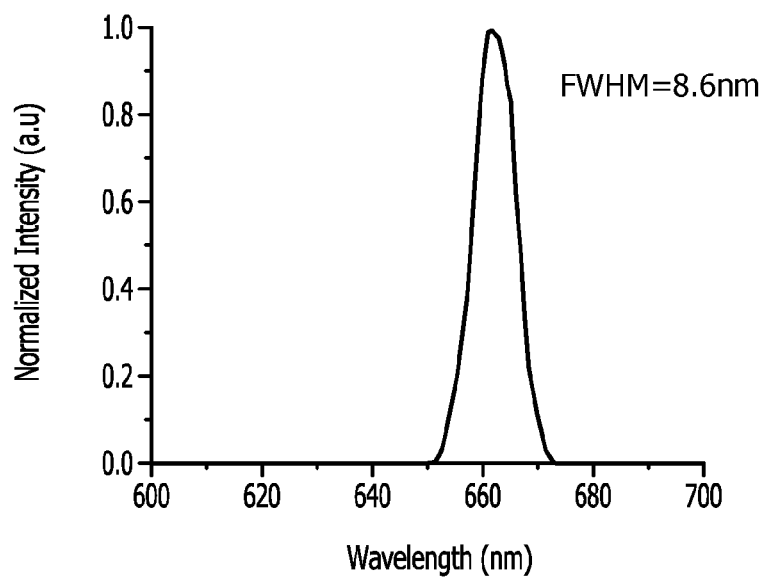

Despite the phase mismatch between the frequency components, we observed significant anti-Stokes generation in the fibers. The spectral content of the anti-Stokes shifted radiation is shown in the graphs of FIGS. 9*a* and 9*b*. Anti-Stokes four-wave-mixing signal measured at the output of the large area core photonic crystal fiber output as shown in FIG. 9*a* and the silica SMF as shown in FIG. 9*b*. The isolated anti-Stokes component shows a well-defined spectral profile that corresponds to the spectral convolution of the pump and Stokes pulse spectra. Because no additional broadening of this shifted component is observed, we conclude that this contribution is generated directly through a nonlinear mixing process between the pump and the Stokes pulses, and thus independent of the self-phase modulation (SPM) mechanism.

Importantly, we observed an identical anti-Stokes component in the case of the silica SMF, confirming that the anti-Stokes shifted this component is not the result of accidental phase matching in the PCF fiber. We verified that the intensity of the anti-Stokes component scales quadratically with the pump light and linearly with the Stokes radiation, confirming that this shifted contribution is the result of a four-wave-mixing process.

FWM/CARS in fibers using two pump beams of different color is a well-known mechanism of generating new frequency components around the zero dispersion wavelength. However, such mechanisms typically rely on phase-matched conditions and the limited width of the Raman gain spectrum in silica, resulting in only moderate spectral shifts (<600 cm$^{-1}$) relative to the input beams. Specially tailored PCFs with exceptionally broad phase-matching conditions have been used to achieve FWM/CARS generation of components shifted as much as 3000 cm$^{-1}$. Large shifts under nonphase matching conditions can be achieved through cascaded stimulated Raman scattering, producing an array of periodically spaced spectral components. Such spectral patterns are not observed in our experiments, suggesting that stimulated Raman processes based on the fundamental Si—O modes are not the primary source of the observed anti-Stokes radiation. A possible explanation for the observed FWM/CARS component is the population of higher lying vibrational states of Si—O overtones and fiber impurities through stimulated Raman pumping, followed by incoherent anti-Stokes scattering by the pump. The incoherent anti-Stokes light is sustained in the fiber as it is not affected by phase-matching with the pump and Stokes beam.

Figure 10A:
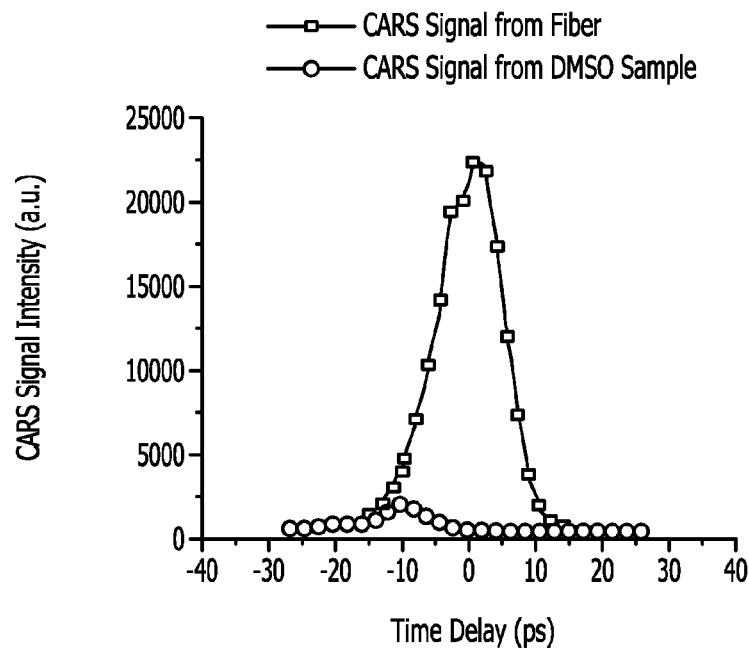
FIG. 10a is a graph of the CARS signal intensity as a function of the time delay between the pump and the Stokes beam in a DMSO sample and from a DCPCF16 fiber.
Figure 10B:
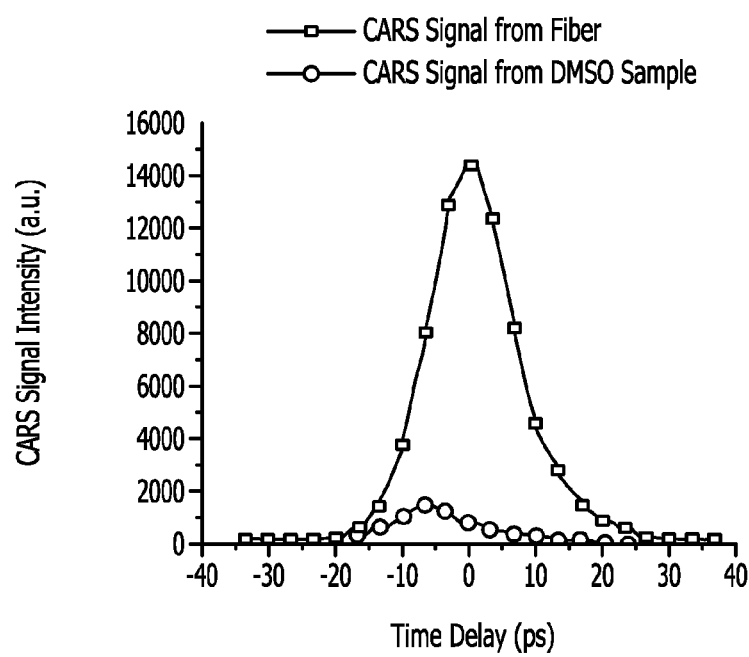
FIG. 10b is a graph of the CARS signal intensity as a function of the time delay between the pump and the Stokes beam in a DMSO sample and from a LMA-20 fiber.

We compared the strength of the anti-Stokes FWM/CARS signal to the CARS signal generated in a dimethyl sulfoxide (DMSO) sample 50 after the fiber. The comparison between the two signals as a function of the time delay between the pump and the Stokes pulses is presented in FIGS. 10*a* and 10*b* for the DC PCF and for the LMA RCF respectively. FIGS. 10*a* and 10*b* are graphs of the CARS signal intensity verses time delay between the pump and the Stokes beam in the DMSO sample and from the DCPCF17 fiber and LMA-20 fiber respectively. A two meter long DC PCF was also used in an effort to separate the fiber anti-Stokes component from the CARS signal generated in the fiber due to a longer walk-off distance of the pump and Stokes propagating pulses. However, we found this measure to be ineffective: the FWM/CARS signal from the fiber could not be sufficiently suppressed without significantly affecting the CARS signal generated in the sample.

Given the observed fiber nonlinearities, we have chosen to use a photonic crystal fiber due to its favorable dispersion properties relative to a standard single mode optical fiber. The presence of intrinsic anti-Stokes generation in the fiber necessitates spectral filtering of the excitation light before focusing it into the sample. We have, therefore, chosen to implement separate fibers for delivery of the excitation light and collection of the signal. We selected the large area PCF (LMA20) for laser pulse delivery because of its excellent suppression of spectral broadening effects. The objective used for fiber coupling provided a coupling efficiency of 40% for 817 nm and 20% for 1074 nm. Since maximum efficiency of this fiber corresponds to 780 nm, a higher coupling efficiency for 817 nm than for 1074 nm was expected. The anti-Stokes radiation generated in the fiber 38 was filtered out by the dichroic mirror placed after the fiber.

The back-scattered forward generated CARS signal in the sample was collected by a second fiber 34. The collection fiber 34 was chosen to be a large mode area, multi-mode fiber for maximum collection. A collection efficiency of 80% was obtained by matching the 0.39 NA of the fiber with the 0.4 NA of the objective used for fiber coupling. To assess the performance of our fiber-delivered probe for CARS imaging, we imaged three different biological tissues ex vivo. We chose to take images of skin and eyelid, superficial tissues that would be easy to access in future in-vivo imaging. Subcutaneous fat (FIG. 11*a*), individual adipocytes (FIG. 11*b*) and meibocytes (FIG. 11*c*) are clearly resolved with high contrast. The contrast observed is comparable to the contrast seen in CARS images obtained through free-space detection of the back-scattered light. This suggests that the detected signal includes the back-scattered, forward generated CARS radiation, and that the contrast is not dominated by aperture effects at the detection fiber. In addition, the contrast is not affected by spurious anti-Stokes components from the delivery fiber, resulting in images that originate solely from CARS generation in the tissue. FIGS. 11*a*-11*c* are CARS microscopic images of thick tissue samples ex vivo, namely Small adipocytes of mouse ear skin in FIG. 11*a*, adipocytes of subcutaneous layer of rabbit skin tissue in FIG. 11*b*, and meibomian gland in mouse eyelid in FIG. 11*c*. Images were acquired in 2 s. Scale bar is 60 μm.

Thus, it may now be appreciated that a fiber-delivered probe suitable for CARS imaging of thick tissues is practical. The disclosed design is based on two advances. First, we identified that a major problem in CARS probe design is the presence of a very strong anti-Stokes component in silica delivery fibers generated through a FWM process. Without proper spectral filtering, this component affects the CARS image from the tissue sample. The illustrated embodiments of the invention efficiently suppress this spurious anti-Stokes component through the use of a separate fiber for excitation delivery and for signal detection, which allows the incorporation of dichroic optics for anti-Stokes rejection. Second, the detection of backscattered CARS radiation from the sample is optimized by using a large core multi mode fiber in the detection channel. This scheme produces high quality CARS images free of detector aperture effects. Miniaturization of this fiber-delivered probe results in a practical handheld probe for clinical CARS imaging.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following invention and its various embodiments.

Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations. A teaching that two elements are combined in a Claimed combination is further to be understood as also allowing for a claimed combination in which the two elements are not combined with each other, but may be used alone or combined in other combinations. The excision of any disclosed element of the invention is explicitly contemplated as within the scope of the invention.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

We claim:

1. A method for using a fiber-based probe and/or fiber-based endoscope for coherent anti-Stokes Raman scattering (CARS) imaging of a sample comprising:
   delivering Stokes and pump excitation beams to a fiber for scanned delivery to the sample;
   eliminating fiber-generated four-wave mixing radiation by removing the fiber-generated four-wave mixing radiation before the Stokes and pump excitation beams are delivered to the sample;
   collecting the CARS signal backscattered from the sample; and
   returning the CARS signal to a detector by utilizing a different portion of the fiber for the CARS signal or by utilizing a different fiber for the CARS signal.

2. The method of claim 1 for coherent anti-Stokes Raman scattering (CARS) imaging further comprising multimodal imaging with second harmonic generation and two-photon excited fluorescence imaging.

3. The method of claim 1 where collecting the CARS signal backscattered from the sample comprises collecting the CARS signal in a fiber separate from the fiber through which the Stokes and pump excitation beams are delivered, or a separate portion of the fiber through which the Stokes and pump excitation beams are delivered.

4. The method of claim 1 where eliminating fiber-generated four-wave mixing radiation comprises suppressing the four-wave mixing radiation through the use of a dichroic beam splitter disposed at the distal end of the fiber-based probe and/or fiber-based endoscope for anti-Stokes rejection.

5. The method of claim 1 where returning the CARS signal to a detector by utilizing a different portion of the fiber for the CARS signal or by utilizing a different fiber for the CARS signal comprises using a large core multimode fiber to transmit the CARS signal to the detector.

6. The method of claim 1 further comprising performing label-free tissue imaging in-situ, endoscopic imaging to determine myelin degradation in the nervous system and the role of lipid in mammary tumorigenesis and atherosclerosis, assessing skin damage assessment to provide a quantitative measure of the density of structural protein in the dermis and the level of skin hydration to provide a real time assessment of skin health of human subjects, performing dry eye syndrome diagnosis to establish whether patients with dry eyes are suffering from dry eye syndrome (DES) for a direct diagnosis of DES, performing food analysis for inspecting the quality of surfaces of food items, performing inspection of photoresists for quality control of thin polymer films, imaging and diagnosing vascular diseases with intravascular CARS imaging and multimodal imaging, or imaging and diagnosing cancers with endoscopic CARS imaging and multimodal imaging.

7. An apparatus comprising: a source of a Stokes and pump excitation beam; a delivery fiber optically coupled to the source; a dichroic beam splitter optically coupled to the delivery fiber, any fiber-generated four-wave mixing radiation being suppressed before the Stokes and pump excitation beams are delivered; a scanner for scanning a transmission beam from the dichroic beam spotter into a sample; optics for collecting backscattered anti-Stokes signal_from the sample; a collection fiber optically coupled to the optics; and a detector optically coupled to the collection fiber to detect the backscatter anti-Stokes signal four-wave mixing radiation; where the delivery fiber comprises a double clad large area core photonic crystal fiber having a core, an inner clad and an outer clad, where the core suppresses the four-wave mixing radiation and where the inner clad transmits the anti-Stokes signal four-wave mixing radiation.

8. The apparatus of claim 7 where the delivery fiber and collection fiber comprise separate optical fibers.

9. The apparatus of claim 7 where the delivery fiber and collection fiber comprise separate portions of the same optical fiber.

10. The apparatus of claim 7 where the core comprises a core which is doped to absorb and filter out the four-wave mixing radiation.

11. The apparatus of claim 7 where the core comprises a thin film coated on a distal end of the core that filters out the four-wave mixing radiation.

12. The apparatus of claim 7 where the core comprises a device that redirects the four-wave mixing radiation.

13. The apparatus of claim 12 where the device comprises a fiber Bragg grating to reflect the four-wave mixing radiation.

14. The apparatus of claim 7 where the core comprises a filter segment that filters out the four-wave mixing radiation.

15. The apparatus of claim 7 further comprising a transparent endoscopic tube in which the delivery fiber and collection fiber and scanner are disposed, and means for rotating the delivery fiber and collection fiber, where the scanner comprises a GRIN lens optically coupled to the delivery fiber and collection fiber and a prism optically coupled to the GRIN lens for side scanning through a distal end of the tube.

16. The apparatus of claim 7 further comprising a transparent endoscopic tube in which the delivery fiber and collection fiber and scanner are disposed, a GRIN lens optically coupled to the delivery fiber and collection fiber and a prism optically coupled to the GRIN lens for side scanning through a distal end of the tube, and where the scanner comprises a motor for rotating the prism.

17. The apparatus of claim 16 further comprising a linear translational motor coupled to the delivery fiber and collection fiber for translating the delivery fiber and collection fiber within the tube.

18. The apparatus of claim 7 further comprising a transparent endoscopic tube in which the delivery fiber and collection fiber and scanner are disposed, where the delivery fiber comprises a filter for suppressing four-wave mixing radiation, and where the scanner comprises a mirror, a MEMS scanner for moving the mirror and a lens optically coupled to the mirror.

19. The apparatus of claim 7 where the delivery fiber and collection fiber comprise:
- a fiber bundle having a central fiber for transmission of the Stokes signal, and the pump signal, and suppression of the four-wave mixing radiation; and
- a plurality of outer fibers for transmission of the anti-Stokes signal.

* * * * *